United States Patent [19]

Bózsing et al.

[11] Patent Number: 5,071,849
[45] Date of Patent: Dec. 10, 1991

[54] DIHYDROPYRIMIDOTHIAZINE DERIVATIVES

[75] Inventors: Dániel Bózsing; Lujza Petőcz; Mária Szécsey née Hegedűs; Péter Tömpe; Gábor Gigler; István Gacsályi; István Gyertyán, all of Budapest, Hungary

[73] Assignee: Egis Gyogyszergyar, Hungary

[21] Appl. No.: 555,943

[22] Filed: Jul. 19, 1990

[30] Foreign Application Priority Data

Jul. 19, 1989 [HU] Hungary .............................. 3658/89
Jul. 19, 1989 [HU] Hungary .............................. 3659/89

[51] Int. Cl.$^5$ .................... C07D 515/04; A61K 31/54
[52] U.S. Cl. .................................... 514/224.2; 544/48
[58] Field of Search ........................ 544/48; 514/224.2

[56] References Cited

PUBLICATIONS

Kappe et al., "Synthesis and Reactions, etc." CA 111:174056y (1989).

*Primary Examiner*—Patricia L. Morris
*Attorney, Agent, or Firm*—Ostrolenk, Faber, Gerb & Soffen

[57] ABSTRACT

The invention relates to new dihydropyrimidothiazine derivatives, a process for the preparation thereof, pharmaceutical compositions comprising the same and new intermediates useful in the preparation of the said dihydropyrimidothiazine derivatives.

The new dihydropyrimidothiazine derivatives of the general formula I,

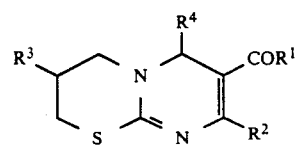

wherein
$R^1$ represents $C_{1-6}$ alkoxy, amino or phenylamino,
$R^2$ stands for $C_{1-6}$ alkyl or phenyl,
$R^3$ represents hydrogen or $C_{1-6}$ alkyl, and
$R^4$ denotes $C_{1-11}$ alkyl or phenyl optionally bearing one or more identical or different substituent/s/ selected from halogen, nitro, amino, di-($C_{1-6}$ alkyl)-amino, $C_{1-6}$ alkyl, $C_{1-6}$ alkoxy and hydroxy, and pharmaceutically acceptable acid addition salts thereof exert valuable antianginal and/or antiinflammatory effect/s/ and are useful in therapy.

5 Claims, No Drawings

DIHYDROPYRIMIDOTHIAZINE DERIVATIVES

This invention relates to new dihydropyrimidothiazine derivatives, a process for the preparation thereof, pharmaceutical compositions comprising the same and new intermediates useful in the preparation of the said dihydropyrimidothiazine derivatives and also a process for the preparation of the said intermediates.

In Belgian patent No. 752,863 dihydropyrimidothiazine derivatives unsubstituted in position 7 are disclosed. These compounds are reported to have antiinflammatory properties.

The 7-substituted dihydropyrimidothiazine derivatives according to this invention, however, in addition to the antiinflammatory effect possess valuable antianginal effect accompanied by diuretic properties. Furthermore, they possess effects on the central nervous system (tranquillant-sedative and/or antidepressant and spasmolytic) and in case of certain compounds they show week positive inotropic or acid-secretion inhibiting properties.

It is an object of the present invention to provide new dihydropyrimidothiazine derivatives of the general Formula I,

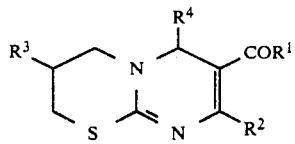

wherein
$R^1$ represents $C_{1-6}$ alkoxy, amino or phenylamino,
$R^2$ stands for $C_{1-6}$ alkyl or phenyl,
$R^3$ represents hydrogen or $C_{1-6}$ alkyl, and
$R^4$ denotes $C_{1-11}$ alkyl or phenyl optionally bearing one or more identical or different substituent(s) selected from halogen, nitro, amino, di-($C_{1-6}$alkyl)-amino, $C_{1-6}$ alkyl, $C_{1-6}$ alkoxy and hydroxy,
and pharmaceutically acceptable acid addition salts thereof.

The term "alkyl" used throughout the specification relates to straight or branched chained saturated aliphatic hydrocarbon groups (e.g. methyl, ethyl, n-propyl, isopropyl, n-butyl etc.). The "alkoxy" groups are alkyl ether groups comprising the above-defined alkyl groups (e.g. methoxy, ethoxy, tert.butoxy etc.). The term "halogen" encompasses the fluorine, chlorine, bromine and iodine atoms. The dialkylamino groups comprise $C_{1-6}$ alkyl groups as defined above (e.g. dimethylaminomethyl, dimethylaminoethyl, dimethylaminopropyl, diethylaminoethyl, diethylaminopropyl etc.).

Compounds of the general Formula I, wherein $R^1$ stands for methoxy, ethoxy or amino, $R^2$ denotes methyl or phenyl, $R^3$ stands for hydrogen, and $R^4$ represents methyl or phenyl whereby the latter carries one or more identical or different methoxy, halogeno or nitro substituent(s), and pharmaceutically acceptable acid addition salts thereof possess particularly valuable pharmaceutical properties.

Particularly preferred representatives of the compounds of the general Formula I are the following derivatives:
ethyl-[6-(4-dimethylaminophenyl)-8-methyl-3,4-dihydro-2H,6H-pyrimido[2,1-b][1,3]thiazine-7-carboxylate];
methyl-[8-methyl-6-(2-methoxyphenyl)-3,4-dihydro-2H,6H-pyrimido[2,1-b][1,3]thiazine-7-carboxylate];
methyl-[6-(3,4-dichlorophenyl)-8-methyl-3,4-dihydro-2H,6H-pyrimido[2,1-b][1,3]thiazine-7-carboxylate];
methyl-[6-(4-chloro-3-nitrophenyl)-8-methyl-3,4-dihydro-2H,6H-pyrimido[2,1-b][1,3]thiazine-7-carboxylate];
and pharmaceutically acceptable acid addition salts thereof.

The compounds of the general Formula I are organic bases, so they can be transformed into acid addition salts. The pharmaceutically acceptable acid addition salts of the compounds of the general Formula I can be formed with inorganic or organic acids (e.g. hydrohalides such as hydrochlorides or hydrobromides; carbonates, hydrogen carbonates, sulfates, acetates, fumarates, maleates, citrates, ascorbinates, etc.).

According to a further aspect of the present invention there is provided a process for the preparation of the compounds of the general Formula I and pharmaceutically acceptable acid addition salts thereof, which comprises reacting a 4,5,6-trisubstituted 1,2,3,4-tetrahydro-2-pyrimidinethione of the general Formula II,

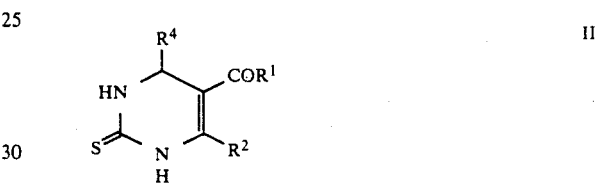

wherein $R^1$, $R^2$ and $R^4$ are as stated above, with a dihalo derivative of the general Formula III,

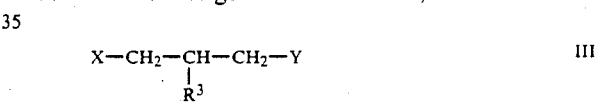

wherein $R^3$ is as stated above and X and Y represent halogen, and, if desired, converting the compound of the general Formula I thus obtained into a pharmaceutically acceptable acid addition salt thereof or setting free a base of the general Formula I from an acid addition salt thereof, or converting an acid addition salt of a base of the general Formula I into another acid addition salt.

The reaction is preferably carried out in an inert organic solvent or in a mixture of such solvents. As reaction medium preferably aliphatic alcohols (e.g. ethanol or isopropanol), dialkyl amides (e.g. dimethylformamide), dialkyl sulfoxides (e.g. dimethyl sulfoxide), chlorinated aliphatic hydrocarbons (e.g. chloroform, carbon tetrachloride, methylene dichloride), aromatic hydrocarbons (e.g. benzene, toluene, xylene), aliphatic or alicyclic ethers (e.g. diethyl ether, tetrahydrofuran, dioxane), aliphatic ketones (e.g. acetone or methyl ethyl ketone) or mixtures thereof can be used. The reaction can very preferably be carried out in dimethylformamide or in a mixture of dimethylformamide and methyl ethyl ketone, or dimethylformamide and acetone.

The reaction can be carried out in the presence of an acid-binding agent. For this purpose e.g. alkali carbonates (e.g. sodium or potassium carbonate), alkali hydrogen carbonates (e.g. sodium or potassium hydrogen carbonate), alkali hydroxides (e.g. sodium or potassium hydroxide), alkaline earth metal hydroxides (e.g. calcium hydroxide) or tertiary amines (e.g. pyridine, triethyl amine or an other trialkyl amine) can be used.

Sodium carbonate and potassium carbonate are particularly useful as acid binding agent.

To accelerate the reaction preferably a catalyst is used. As catalyst e.g. alkali halides (e.g. potassium iodide, potassium fluoride, sodium bromide) and alkali earth metal halides (e.g. calcium chloride) can be used. It is particularly preferred to use potassium iodide as catalyst.

The reaction temperature depends on the reactivity of the starting materials. One may work generally at a temperature between room temperature and the boiling point of the reaction mixture, preferably at a temperature of 70° to 80° C. The reaction time depends on the activity of the starting materials used and the reaction time is generally about 5 to 36 hours.

The starting compounds of the general Formulae II and III can be used in equimolar amounts, or the dihalo derivative of the general Formula III is used in an excess of not more than 0.5 mole. The acid-binding agent may be applied in equimolar amount or in an excess of 1 mole. The catalyst can be used in an amount of 0.1 to 0.2 mole. Preferably 0.1 mole of catalyst is used.

The reaction mixture can be worked up by methods known per se. The product is preferably isolated by filtering off the precipitated inorganic salts and distilling off the solvent in vacuo. The residue can be crystallized from water or from an organic solvent. If necessary, the product thus obtained can be subjected to further purification (e.g. recrystallization or chromatography).

The compounds of the general Formula I can be isolated in form of pharmaceutically acceptable acid addition salts, too, or the bases of the general Formula I can be converted into acid addition salts in a further reaction step by reacting them with the corresponding inorganic or organic acid in an inert solvent. The bases of the general Formula I can be set free again from the acid addition salts by treating them with a base in a manner known per se, and, if desired, they can be converted into other acid addition salts.

The starting compounds of the general Formula III are known and commercially available products.

The 4,5,6-trisubstituted derivatives of the general Formula II, wherein $R^4$ represents an optionally substituted phenyl as defined above, are known compounds (published Japanese patent application No. 59,190,974 or European patent application No. 202,654).

The 4,5,6-trisubstituted 1,2,3,4-tetrahydro-2-pyrimidinethione derivatives, wherein $R^4$ represents $C_{1-11}$ alkyl, are new compounds.

According to a further aspect of the present invention there are provided new intermediates of the general Formula II, wherein $R^4$ represents $C_{1-11}$ alkyl and $R^1$ and $R^2$ are as stated above.

According to a further aspect of the present invention there is provided a process for the preparation of compounds of the general Formula II, which comprises reacting an aldehyde of the general Formula IV, $$R^4\text{-CHO} \qquad \text{IV}$$

wherein $R^4$ is a $C_{1-11}$ alkyl, with a beta-ketocarboxylic acid derivative of the general Formula V,

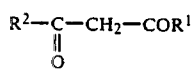 V wherein $R^1$ and $R^2$ are as stated above, and with thiourea.

The starting materials can be reacted in an inert organic solvent or in the mixture thereof. For this purpose aliphatic alcohols (e.g. ethanol or isopropanol), dialkyl amides (preferably dimethylformamide), dialkyl sulfoxides (preferably dimethyl sulfoxide), chlorinated aliphatic hydrocarbons (e.g. chloroform, carbon tetrachloride, methylene dichloride), aromatic hydrocarbons (e.g. benzene, toluene or xylene), aliphatic or alicyclic ethers (e.g. diethyl ether, tetrahydrofuran, dioxane) or a mixture of at least two of the above solvents can be used.

To accelerate the reaction a catalyst can be applied. Gaseous hydrogen chloride—either anhydrous or absorbed in an organic solvent—may serve as catalyst. It is preferable to use hydrogen chloride absorbed in isopropanol as catalyst.

The reaction is carried out at a temperature between 10° C. and 50° C., preferably at room temperature. The reaction time depends on the activity of the starting materials and varies between 3 and 35 hours.

The starting compounds of the general Formulae IV and V and the thiourea are preferably used in equimolar amounts, or the thiourea is used in an excess of 0.1 to 1 mole.

The catalyst may be used in a 1 to 7 molar equivalent(s) amount related to one mole of the compound of the general Formula IV.

The reaction mixture can be worked up by methods known per se. The product thus obtained can be isolated by filtration, or the solvent is evaporated and the residue is crystallized from water or from an organic solvent and the suspension thus obtained is filtered.

The starting materials are known compounds and readily available commercial products.

The compounds of the general Formula I possess valuable antianginal and antiinflammatory properties supplemented by diuretic effect. Furthermore, they affection the central nervous system. Taking into consideration that in case of anginal diseases the inducing factors are often of neurotic origin or they appear on patients suffering from ischuria, sedative or vitalizing effect accompanied by diuretic properties represents a more complex therapy.

The compounds of the general Formula II also show antianginal properties which are supplemented by an analgesic effect.

The activity of the compounds of the invention are examined by the following tests.

1. ACUTE TOXICITY ON MICE

White mice belonging to the CFLP strain (body weight 18–22 g; both male and female) are used, 10 animals for each dose. The test compound is administered orally in a volume of 20 ml/kg. After treatment the animals are observed for a period of 14 days. The mice are kept in a plastic cage at room temperature. The animals get tap water and standard mouse fodder ad libitum. The toxicity data are determined with the aid of the method of Litchfield and Wilcoxon (Litchfield, J. T., Wilcoxon, F. W.: J. Pharmacol. Exp. Ther., 96, 99 (1949)). The results are summarized in Table 1.

TABLE I

| Acute toxicity on mice | |
|---|---|
| Example No. | LD$_{50}$ mg/kg p.o. |
| 1 | 580 |

TABLE I-continued

| Acute toxicity on mice | |
|---|---|
| Example No. | $LD_{50}$ mg/kg p.o. |
| 2 | 170 |
| 3 | 1000 |
| 4 | 370 |
| 5 | 700 |
| 6 | >1000 |
| 7 | 600 |
| 8 | 700 |
| 9 | >1000 |
| 10 | >1000 |
| 11 | >1000 |
| 12 | >1000 |
| 13 | 1000 |

2. ANTIANGINAL EFFECT

Method

The test was carried out on rats by using the method of Nieschulz, E., Popendiker, K. and Hoffmann, I. (Arzneimittel Forschung, 5, 680 (1955)). Male rats of 180-220 g body weight were narcotised with chloralese-urethane (70/700 mg/kg ip.). The ECG was registered with needle electrodes in standard II leading. The experimental coronaria insufficiency was induced with vasopressin (4 NE/kg i.v.). The height of wave T in ECG was measured before and after the administration of vasopressin in both the control and treated groups. Test compounds were administered intravenously 2 minutes prior to the treatment with vasopressin. The results are summarized in Table II.

TABLE II

| Test compound /Example No./ | Antianginal effect | |
|---|---|---|
| | Activity (2 mg/kg iv.) | $ED_{50}$ mg/kg /iv./ |
| 8 | −71 | 1.21 |
| 7 | −51 | 1.87 |
| 19 | −51 | 1.45 |
| 6 | −48 | |
| 12 | −40 | |
| 2 | −30 | |
| 15 | −40 | |
| 16 | −57 | about 0.81 |
| 30 | −43 | |
| 31 | −30 | |
| 36 | −32 | |
| Prenylamine | −32 | 6.5 |

As the above data show, the most effective compounds of the present invention exhibit an antianginal effect which is 3 to 8 times higher than that of Prenylamine.

3. ANTIINFLAMMATORY EFFECT

Method

The antiinflammatory effect of the novel compounds of the invention was investigated on rats weighing 150 to 180 g. 0.1 ml of a 1 per cent carrageen suspension was injected subcutaneously into the plantar region of one of the hind paws. Rats were fasted for 12 hours and received drinking water ad libitum. One hour before treatment with the test compound animals were hydrated orally with 30 ml/kg of tap water. The test compounds or the vehicle were administered p.o. in a volume of 10 ml/kg, then two hours later carrageen was applied. The volume of the treated paw was measured by mercury-plethysmometer before and 3 hours after injection in such a way that displacement of the liquid arising from the volume alteration was indicated on a millimeter scale. The volumes of the treated paws were compared with those of the control group. The dose resulting in an inhibition of 30% ($ID_{30}$) was determined by the aid of a line of regression. The results are given in Table III.

TABLE III

| Inhibition of carrageen - induced oedema on rats | | | |
|---|---|---|---|
| Test compound /Example No./ | $LD_{50}$ (mg/kg) | $ID_{30}$ (mg/kg) | Therapeutical index |
| 25 | 100-500 | 10 | 10-50 |
| 14 | 400 | 10 | 40 |
| 15 | >1000 | 70 | >14.3 |
| 16 | 1000 | 120 | 8.3 |
| 18 | >1000 | 110 | >9.1 |
| 22 | 700 | 10 | 70 |
| Indomethacin | 22.5 | 3 | 7.3 |
| Phenylbutazone | 1000 | 40 | 25 |
| Acetylsalicylic acid | 1350 | 200 | 6.8 |
| Paracetamol | 1180 | 200 | 5.9 |

The compounds of the general Formula I are superior to the reference compounds concerning both the absolute dose and the therapeutical index.

4. HEXOBARBITAL NARCOSIS ON MICE

Method

Groups consisting of 6 mice are used for each dose. The animals are treated orally with the test compound, whereby sleeping is induced 1 hour later by administering a 40 mg/kg i.v. dose of Hexobarbital both to the test and control groups.

EVALUATION

Animals which have a sleeping time more than 2.5 times longer than that of the control group are considered to show a positive reaction. $ED_{50}$ values are calculated from the thus-transformed data. (Kaergaard Nielsen C. et al., Arch. Int. Pharmacodyn. 2, 170 (1967)). The results are summarized in Table IV.

TABLE IV

| Hexobarbital narcosis on mice | | |
|---|---|---|
| Test compound /Example No./ | $ED_{50}$ (mg/kg p.o.) | Therapeutical index |
| 13 | about 200 | 5.0 |
| 10 | 39 | 25.6 |
| 6 | 25 | 40.0 |
| 11 | about 200 | 5.0 |
| Meprobamate | 260 | 4.2 |

The compounds of the general Formula I are superior to the reference substance Meprobamate regarding both the absolute dose and the therapeutical index. The narcosis-potentiating effect is accompanied by a weak motility-inhibiting effect.

According to a further aspect of the present invention there are provided pharmaceutical compositions comprising as active ingredient at least one compound of the general Formula I or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potatoe starch, talc, magnesium carbonate, magnesium stearate, calcium carbonate, stearic acid or the salts thereof, etc. can be used. As carrier for the soft gelatine capsules e.g. vegetable oils, fats, waxes or polyols of suitable consistency can be used. As carriers for the solutions and syrups e.g. water, polyols (polyethylene glycol), sacharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers, etc. The pharmaceutical formulations may further comprise other active ingredients which do not exhibit synergistic effect together with the compounds of the general Formula I.

The compounds of the general Formula I can preferably be used in therapy orally in the form of tablets or capsules. Especially preferred are the capsules or tablets comprising 0,5 to 100 mg of active ingredient.

The daily dose of the compounds of the general Formula I can vary within wide ranges depending on several factors, e.g. on the activity of the active ingredient, the patient's condition and age, the severity of the disease, etc. The preferred oral dose is generally 2 to 500 mg/day. It has to be stressed that the above dose is only of informative character and the administered dose must always be determined by the physician therapeutist.

According to a further aspect of the present invention there is provided the use of the compounds of the general Formula I or pharmaceutically acceptable salts thereof for the preparation of pharmaceutical compositions having particularly antianginal and antiinflammatory effects.

According to a still further aspect of the present invention there is provided a method of antianginal or antiinflammatory treatment, which comprises administering to the patient an effective amount of a compound of the general Formula I or a pharmaceutically acceptable salt thereof.

The invention is further illustrated by the following Examples of non-limiting character.

EXAMPLE 1

Ethyl-(6-phenyl-8-methyl-3,4-dihydro-2H,6H-pyrimido-[2,1-b][1,3]thiazine-7-carboxylate), furthermore the hydrobromide and hydrochloride thereof 27.6 g (0.1 mole) of ethyl-(4-phenyl-6-methyl-1,2,3,4-tetrahydro-2-pyrimidinethione-5-carboxylate) (and 30.3 g (0.15 mole) of 1,3-dibromopropane) are refluxed in the mixture of 500 ml of methyl ethyl ketone and 50 ml of dimethylformamide, in the presence of 27.6 g (0.2 mole) of potassium carbonate and 2.0 g (0.012 mole) of potassium iodide for 15 hours. The reaction mixture is allowed to cool to room temperature, filtered and the filtrate is evaporated. The residue is crystallized from ethyl acetate, filtered and dried.

Thus 25.8 g (65%) of the hydrobromide salt of the desired compound are obtained.

M.p.: 192° to 194° C.

The hydrobromide salt thus obtained is dissolved in 530 ml of water, and the solution is adjusted to pH 7 with a sodium bicarbonate solution. The precipitated crystals are filtered off, washed with water and dried.

Thus 19.5 g (95%) of the desired compound are obtained in the form of free base.

M.p.: 110° to 112° C.

The base thus obtained is dissolved in 225 ml of ethyl acetate, and an ethyl alcohol solution containing an equimolar amount of hydrogen chloride is dropped to it. The reaction mixture is stirred for 1 hour, the suspension is cooled, filtered, washed with ethyl acetate and dried.

Thus 21.3 g of the hydrochloride of the desired compound are obtained.

Analysis for the Formula $C_{17}H_{20}N_2O_2S \cdot HCl$ (352.879): Calculated: C %=57.68; H %=6.0; N %=7.94; S %=9.08; Cl⁻%=10.05. Found: C %=58.87; H %=6.17; N %=7.87; S %=9.18; Cl⁻%=10.25.

EXAMPLE 2

Ethyl-[6-(2-fluoro-6-chlorophenyl)-8-methyl-3,4-dihydro-2H,6H-pyrimido[2,1-b][1,3]thiazine-7-carboxylate]

32.9 g (0.1 mole) of ethyl-[4-(2-fluoro-6-chlorophenyl)-6-methyl-1,2,3,4-tetrahydro-2-pyrimidinethione-5-carboxylate] and 30.3 g (0.15 mole) of 1,3-dibromopropane are reacted as described in Example 1 for 20 hours. The residue is crystallized from water, filtered and dried.

Thus 35 g (94.9%) of the desired compound are obtained.

M.p.: 129° to 131° C.

Analysis for the Formula $C_{17}H_{18}ClFN_2O_2S$ (368.855): Calculated: C %=55.36; H %=4.92; N %=7.59; S %=8.69; Cl %=9.61. Found: C %=55.82; H %=5.00; N %=7.57; S %=8.76; Cl %=9.57.

EXAMPLE 3

Ethyl-[6-(3,4-dichlorophenyl)-8-methyl-3,4-dihydro-2H,6H-pyrimido[2,1-b][1,3]thiazine-7-carboxylate]

34.5 g (0.1 mole) of ethyl-[4-(3,4-dichlorophenyl)-6-methyl-1,2,3,4-tetrahydro-2-pyrimidinethione-5-carboxylate] and 30.3 g (0.15 mole) of 1,3-dibromopropane are reacted as described in Example 1 for 26 hours. The residue is crystallized from water, filtered and dried.

Thus 37 g (97.0%) of the desired compound are obtained.

M.p.: 116° to 118° C.

Analysis for the Formula $C_{17}H_{18}NCl_2N_2O_2S$ (385.315): Calculated: C %=52.99; H %=4.71; N %=7.27; S %=8.32; Cl %=18.40. Found: C %=52.71; H %=4.71; N %=7.27; S %=8.32; Cl %=18.40.

EXAMPLE 4

Methyl-[6-(3-nitrophenyl)-8-methyl-3,4-dihydro-2H,6H-pyrimido[2,1-b][1,3]thiazine-7-carboxylate]

30.7 g (0.1 mole) of methyl-[4-(3-nitrophenyl)-6-methyl-1,2,3,4-tetrahydro-2-pyrimidinethione-5-carboxylate] and 30.3 g (0.15 mole) of 1,3-dibromopropane are reacted as described in Example 1 for 13 hours. The residue is crystallized from water, filtered and dried.

Thus 29.2 g (84%) of the desired compound are obtained.

M.p.: 178° to 180° C.

Analysis for the Formula $C_{16}H_{17}N_3O_4S$ (347.391): Calculated: C %=55.32; H %=4.93; N %=12.09; S %=9.23. Found: C %=55.27; H %=4.86; N %=12.03; S %=9.11.

EXAMPLE 5

6-Phenyl-8-methyl-3,4-dihydro-2H,6H-pyrimido[2,1-b][1,3]thiazine-7-carboxylic anilide and the hydrochloride thereof 32.3 g (0.1 mole) of 4-phenyl-6-methyl-1,2,3,4-tetrahydro-2-pyrimidinethione-5-carboxylic anilide and 30.3 g (0.15 mole) of 1,3-dibromopropane are reacted as described in Example 1 for 6 hours. The residue is crystallized from ethyl alcohol, filtered and dried.

Thus 21.8 g (60%) of the desired compound are obtained.

M.p.: 222° to 224° C.

18.2 g of the base thus obtained are suspended in ethyl acetate, and an ethyl alcohol solution containing an equimolar amount of hydrogen chloride is dropped to it. The suspension is stirred for one hour, then cooled to 5° C., filtered, washed with ethyl acetate and dried.

Thus 17.6 g (88%) of the hydrochloride salt of the desired compound are obtained.

M.p.: 206° to 209° C.

Analysis for the Formula $C_{21}H_{21}N_3O_6 \cdot HCl$ (399.938): Calculated: C %=63.07; H %=5.54; N %=10.51; S %=8.02; Cl⁻%=8.86. Found: C %=62.59; H %=5.69; N %=10.20; S %=7.84; Cl⁻%=8.75.

EXAMPLE 6

6-(2-Fluoro-6-chlorophenyl)-8-methyl-3,4-dihydro-2H,6H-pyrimido[2,1-b][1,3]thiazine-7-carboxylic anilide 37.6 g (0.1 mole) of 4-(2-fluoro-6-chlorophenyl)-6-methyl-1,2,3,4-tetrahydro-2-pyrimidinethione-5-carboxylic anilide and 23.2 g (0.115 mole) of 1,3-dibromopropane are reacted in 200 ml of dimethylformamide, in the presence of 13.8 g (0.1 mole) of potassium carbonate at 70° C. for 7 hours. Then it is allowed to cool to room temperature, filtered and the filtrate is evaporated in vacuo. The residue is crystallized from water, filtered and dried. Thus 40.3 g (97%) of the desired compound are obtained.

M.p.: 210° to 215° C.

Analysis for the Formula $C_{21}H_{19}ClFN_3OS$ (415.914): Calculated: C %=60.65; H %=4.60; N %=10.10; S %=7.71; Cl %=8.52. Found: C %=59.68; H %=4.59; N %=9.94; S %=7.71; Cl %=8.49.

EXAMPLE 7

Ethyl-[8-methyl-6-(4-methoxyphenyl)-3,4-dihydro2H,6H-pyrimido[2,1-b][1,3]thiazine-7-carboxylate]

30.6 g (0.1 mole) of ethyl-[6-methyl-4-(4-methoxyphenyl)-1,2,3,4-tetrahydro-2-pyrimidinethione-5-carboxylate] and 30.3 g (0.15 mole) of 1,3-dibromopropane are reacted as described in Example 1 for 13 hours. The residue is crystallized from isopropanol, filtered and dried.

Thus 18 g (52%) of the desired compound are obtained.

M.p.: 148° to 150° C.

Analysis for the Formula $C_{18}H_{22}N_2O_3S$ (346.477): Calculated: C %=62.40; H %=6.40; N %=8.09; S %=9.25. Found: C %=62.33; H %=6.33; N %=8.13; S %=9.10.

EXAMPLE 8

Methyl-[6-(4-chloro-3-nitrophenyl)-8-methyl-3,4-dihydro-2H,6H-pyrimido[2,1-b][1,3]thiazine-7-carboxylate 34.2 g (0.1 mole) of methyl-[4-(4-chloro-3-nitrophenyl)-6-methyl-1,2,3,4-tetrahydro-2-pyrimidinethione-5-carboxylate] and 30.3 g (0.15 mole) of 1,3-dibromopropane are reacted as described in Example 1 for 13 hours. The residue is crystallized from water, filtered and dried.

Thus 37.4 g (98%) of the desired compound are obtained.

M.p.: 146° to 148° C.

Analysis for the Formula $C_{16}H_{16}ClN_3O_4S$ (381.834): Calculated: C %=50.33; H %=4.22; N %=11.0; Cl %=9.28; S %=8.40. Found: C %=49.00; H %=4.33; N %=10.78; Cl %=9.32; S %=8.07.

EXAMPLE 9

Methyl-[3,8-dimethyl-6-(4-chloro-3-nitrophenyl)-3,4-dihydro-2H,6H-pyrimido[2,1-b][1,3]thiazine-7-carboxylate 34.2 g (0.1 mole) of methyl-[4-(4-chloro-3-nitrophenyl)-6-methyl-1,2,3,4-tetrahydro-2-pyrimidinethione-5-carboxylate] and 19.7 g (0.115 mole) of 2-methyl-1,3-chloro-bromopropane are reacted as described in Example 1 for 16 hours. The residue is crystallized from water, filtered and dried.

Thus 29.7 g (75%) of the desired compound are obtained.

M.p.: 139° to 142° C.

Analysis for the Formula $C_{17}H_{18}ClN_3O_4S$ (395.861): Calculated: C %=51.58; H %=4.58; N %=10.61; S %=8.10; Cl %=8.96. Found: C %=51.12; H %=4.46; N %=10.61; S %=8.06; Cl %=8.97.

EXAMPLE 10

Methyl-[3,8-dimethyl-6-(3-nitrophenyl)-3,4-dihydro-2H,6H-pyrimido[2,1-b][1,3]thiazine-7-carboxylate 30.7 g (0.1 mole) of methyl-[4-(3-nitrophenyl)-6-methyl-1,2,3,4-tetrahydro-2-pyrimidinethione-5-carboxylate] and 19.7 g (0.115 mole) of 2-methyl-1,3-chlorobromopropane are reacted as described in Example 6 for 24 hours at 100° C. The residue is crystallized from water, filtered and dried.

Thus 31.4 g (87.1%) of the desired compound are obtained.

M.p.: 145° to 150° C.

Analysis for the Formula $C_{17}H_{18}N_3O_4S$ (360.411): Calculated: C %=56.65; H %=5.03; N %=11.66; S %=8.89. Found: C %=56.78; H %=5.34; N %=11.54; %=9.06.

EXAMPLE 11

Ethyl-[6-(4-bromophenyl)-8-methyl-3,4-dihydro-2H,6H-pyrimido[2,1-b][1,3]thiazine-7-carboxylate]

35.5 g (0.1 mole) of ethyl-[4-(4-bromophenyl)-6-methyl-1,2,3,4-tetrahydro-2-pyrimidinethione-5-carboxylate] and 30.3 g (0.15 mole) of 1,3-dibromopropane are reacted as described in Example 1 for 13 hours. The residue is crystallized from water, filtered and dried.

Thus 28.2 g (71.3%) of the desired compound are obtained.

M.p.: 150° to 153° C.

Analysis for the Formula $C_{17}H_{19}BrN_2O_2S$ (395.393): Calculated: C %=51.65; H %=4.84; N %=7.09; Br %=20.21; S %=8.11. Found: C %=52.00; H %=4.93; N %=7.42; Br %=20.06; S %=7.94.

EXAMPLE 12

Ethyl-[8-phenyl-6-(2-fluoro-6-chlorophenyl)-3,4-dihydro-2H,6H-pyrimido[2,1-b][1,3]thiazine-7-carboxylate 39.1 g (0.1 mole) of ethyl-[6-phenyl-4-(2-fluoro-6-chlorophenyl)-1,2,3,4-tetrahydro-2-pyrimidinethione-5-carboxylate] and 23.2 g (0.115 mole) of 1,3-dibromopropane are reacted as described in Example 6 for 5 hours. The residue is crystallized from water, filtered and dried.

Thus 39.6 g (92%) of the desired compound are obtained.

M.p.: 168° to 170° C.

Analysis for the Formula $C_{22}H_{20}ClFN_2O_2S$ (430.926): Calculated: C %=61.32; H %=4.68; N %=6.50; S %=7.44; Cl %=8.23. Found: C %=60.40; H %=4.64; N %=6.49; S %=7.44; Cl %=8.12.

EXAMPLE 13

Ethyl-[8-phenyl-6-(4-nitrophenyl)-3,4-dihydro-2H,6H-pyrimido[2,1-b][1,3]thiazine-7-carboxylate]

38.3 g (0.1 mole) of ethyl-[6-phenyl-4-(4-nitrophenyl)-1,2,3,4-tetrahydro-2-pyrimidinethione-5-carboxylate] and 30.3 g (0.15 mole) of 1,3-dibromopropane are reacted as described in Example 1 for 6 hours. The residue is crystallized from ethyl alcohol, filtered and dried.

Thus 19.1 g (45%) of the desired compound are obtained.

M.p.: 190° to 192° C.

Analysis for the Formula $C_{22}H_{21}N_3O_4S$ (423.49): Calculated: C %=62.40; H %=5.0; N %=9.92; S %=7.54. Found: C %=62.77; H %=5.06; N %=9.73; S %=7.47.

EXAMPLE 14

Methyl-(6,8-dimethyl-3,4-dihydro-2H,6H-pyrimido[2,1-b][1,3]thiazine-7-carboxylate)

20.0 g (0.1 mole) of methyl-(4,6-dimethyl-1,2,3,4-tetrahydro-2-pyrimidinethione-5-carboxylate) and 30.3 g (0.15 mole) of 1,3-dibromopropane are reacted in the mixture of 500 ml of acetone and 50 ml of dimethylformamide, in the presence of 27.6 g (0.2 mole) of potassium carbonate and 2.0 g (0.012 mole) of potassium iodide for 32 hours at the boiling point of the reaction mixture. Then it is allowed to cool to room temperature, filtered and the filtrate is evaporated. The residue is crystallized from water, filtered and dried.

Thus 19.2 g (80%) of the desired compound are obtained.

M.p.: 92° to 94° C.

Analysis for the Formula $C_{11}H_{16}N_2O_2S$ (240.323): Calculated: C %=54.98; H %=6.71; N %=11.66; S %=13.34. Found: C %=55.37; H %=6.78; N %=11.35; S %=13.22.

EXAMPLE 15

Methyl-[8-methyl-6-(4-methoxyphenyl)-3,4-dihydro-2H,6H-pyrimido[2,1-b][1,3]thiazine-7-carboxylate]

29.2 g (0.1 mole) of methyl-[6-methyl-(4-methoxyphenyl)-1,2,3,4-tetrahydro-2-pyrimidinethione-5-carboxylate] and 30.3 g (0.15 mole) of 1,3-dibromopropane are reacted as described in Example 14 for 36 hours. The residue is crystallized from isopropanol, filtered and dried.

Thus 27.9 g (83.9%) of the desired compound are obtained.

M.p.: 185° to 186° C.

Analysis for the Formula $C_{17}H_{20}N_2O_3S$ (332.43): Calculated: C %=61.42; H %=6.06; N %=8.43; S %=9.64. Found: C %=61.95; H %=6.30; N %=8.40; S %=9.46.

EXAMPLE 16

Methyl-[6-(3,4-dichlorophenyl)-8-methyl-3,4-dihydro-2H,6H-pyrimido[2,1-b][1,3]thiazine-7-carboxylate]

33.1 g (0.1 mole) of methyl-[4-(3,4-dichlorophenyl)-6-methyl-1,2,3,4-tetrahydro-2-pyrimidinethione-5-carboxylate] and 30.3 g (0.15 mole) of 1,3-dibromopropane are reacted as described in Example 14 for 23 hours. The residue is crystallized from water, filtered and dried.

Thus 35.3 g (95%) of the desired compound are obtained.

M.p.: 151° to 152° C.

Analysis for the Formula $C_{16}H_{16}Cl_2N_2O_2S$ (371.288): Calculated: C %=51.76; H %=4.34; N %=7.54; S %=8.63; Cl %=19.10. Found: C %=52.02; H %=4.43; N %=7.62; S %=8.71; Cl %=18.38.

EXAMPLE 17

Ethyl-[8-methyl-6-(3-nitrophenyl)-3,4-dihydro-2H,6H-pyrimido[2,1-b][1,3]thiazine-7-carboxylate]

32.1 g (0.1 mole) of ethyl-[6-methyl-4-(3-nitrophenyl)-1,2,3,4-tetrahydro-2-pyrimidinethione-5-carboxylate] and 30.3 g (0.15 mole) of 1,3-dibromopropane are reacted as described in Example 14 for 30 hours. The residue is crystallized from water, filtered and dried.

Thus 33.6 g (93%) of the desired compound are obtained.

M.p.: 163° to 165° C.

Analysis for the Formula $C_{17}H_{19}N_3O_4S$ (361.419): Calculated: C %=56.49; H %=5.30; N %=11.63; S %=8.87. Found: C %=56.89; H %=5.05; N %=11.48; S %=8.76.

EXAMPLE 18

Methyl-[8-methyl-6-(3,4,5-trimethoxyphenyl)-3,4-dihydro-2H,6H-pyrimido[2,1-b][1,3]thiazine-7-carboxylate]

35.2 g (0.1 mole) of methyl-[6-methyl-4-(3,4,5-trimethoxyphenyl)-1,2,3,4-tetrahydro-2-pyrimidinethione-5-carboxylate] and 30.3 g (0.15 mole) of 1,3-dibromopropane are reacted as described in Example 14 for 32 hours. The residue is crystallized from isopropanol, filtered and dried.

Thus 19.6 g (50%) of the desired compound are obtained.

M.p.: 137° to 138° C.

Analysis for the Formula $C_{19}H_{24}N_2O_5S$ (392.473): Calculated: C %=58.15; H %=6.16; N %=7.14; S % = 8.17. Found: C % = 57.28; H % = 5.96; N % = 7.02; S % = 8.01.

EXAMPLE 19

Ethyl-[8-phenyl-6-(4-methoxyphenyl)-3,4-dihydro-2H,6H-pyrimido[2,1-b][1,3]thiazine-7-carboxylate]

36.8 g (0.1 mole) of ethyl-[6-phenyl-4-(4-methoxyphenyl)-1,2,3,4-tetrahydro-2-pyrimidinethione-5-carboxylate] and 30.3 g (0.15 mole) of 1,3-dibromopropane are reacted as described in Example 1 for 9 hours. The precipitated crystals are filtered off, washed with isopropanol and dried.

Thus 32.7 g (80%) of the desired compound are obtained.

M.p.: 180° to 182° C.

Analysis for the Formula $C_{23}H_{24}N_2O_3S$ (408.518):
Calculated: C % = 67.62; H % = 5.92; N % = 6.86; S % = 7.85. Found: C % = 67.33; H % = 5.90; N % = 6.93; S % = 7.69.

EXAMPLE 20

Methyl-[8-methyl-6-(4-methylphenyl)-3,4-dihydro-2H,6H-pyrimido[2,1-b][1,3]thiazine-7-carboxylate]

27.6 g (0.1 mole) of methyl-[6-methyl-4-(4-methylphenyl)-1,2,3,4-tetrahydro-2-pyrimidinethione-5-carboxylate] and 30.3 g (0.15 mole) of 1,3-dibromopropane are reacted as described in Example 14 for 25 hours. The residue is washed with acetone, filtered and dried.

Thus 24.7 g (78%) of the desired compound are obtained.

M.p.: 184° to 186° C.

Analysis for the Formula $C_{17}H_{20}N_2O_2S$ (316.404):
Calculated: C % = 64.53; H % = 6.37; N % = 8.85; S % = 10.13. Found: C % = 64.67; H % = 6.46; N % = 8.89; S % = 10.11.

EXAMPLE 21

Ethyl-[8-methyl-6-(3,4,5-trimethoxyphenyl)-3,4-dihydro-2H,6H-pyrimido[2,1-b][1,3]thiazine-7-carboxylate 36.6 g (0.1 mole) of ethyl-[6-methyl-4-(3,4,5-trimethoxyphenyl)-1,2,3,4-tetrahydro-2-pyrimidinethione-5-carboxylate] and 30.3 g (0.15 mole) of 1,3-dibromopropane are reacted as described in Example 14 for 28 hours. The residue is crystallized from water, filtered and dried.

Thus 34 g (83.6%) of the desired compound are obtained.

M.p.: 104° to 105° C.

Analysis for the Formula $C_{20}H_{26}N_2O_5S$ (404.480):
Calculated: C % = 59.09; H % = 6.45; N % = 6.89; S % = 7.88. Found: C % = 58.94; H % = 6.50; N % = 6.82; S % = 7.76.

EXAMPLE 22

Ethyl-[6-(4-dimethylaminophenyl)-8-methyl-3,4-dihydro-2H,6H-pyrimido[2,1-b][1,3]thiazine-7-carboxylate]

31.9 g (0.1 mole) of ethyl-[4-(dimethylaminophenyl)-6-methyl-1,2,3,4-tetrahydro-2-pyrimidinethione-5-carboxylate] and 30.3 g (0.15 mole) of 1,3-dibromopropane are reacted as described in Example 14 for 30 hours. The residue is crystallized from water, filtered and dried.

Thus 31.3 g (87.1%) of the desired compound are obtained.

M.p.: 128° to 130° C.

Analysis for the Formula $C_{19}H_{24}N_3O_2S$ (358.335):
Calculated: C % = 63.48; H % = 7.01; N % = 11.69; S % = 8.92. Found: C % = 63.91; H % = 6.97; N % = 11.69; S % = 8.80.

EXAMPLE 23

Ethyl-(6-ethyl-8-phenyl-3,4-dihydro-2H,6H-pyrimido[2,1-b][1,3]thiazine-7-carboxylate)

29 g (0.1 mole) of ethyl-(4-ethyl-6-phenyl-1,2,3,4-tetrahydro-2-pyrimidinethione-5-carboxylate) and 30.3 g (0.15 mole) of 1,3-dibromopropane are reacted as described in Example 14 for 28 hours. The residue is crystallized from water, filtered and dried.

Thus 27 g (81.7%) of the desired compound are obtained.

M.p.: 74° to 76° C.

Analysis for the Formula $C_{18}H_{22}N_2O_2S$ (330.448):
Calculated: C % = 65.43; H % = 6.71; N % = 8.48; S % = 9.70. Found: C % = 64.11; H % = 6.61; N % = 8.33; S % = 9.41.

EXAMPLE 24

Methyl-(6-phenyl-8-methyl-3,4-dihydro-2H,6H-pyrimido[2,1-b][1,3]thiazine-7-carboxylate)

26.2 g (0.1 mole) of methyl-(4-phenyl-6-methyl-1,2,3,4-tetrahydro-2-pyrimidinethione-5-carboxylate) and 30.3 g (0.15 mole) of 1,3-dibromopropane are reacted as described in Example 14 for 17 hours. The residue is crystallized from water, filtered and dried.

Thus 19 g (62.8%) of the desired compound are obtained.

M.p.: 194° to 196° C.

Analysis for the Formula $C_{16}H_{18}N_2O_2S$ (302.393):
Calculated: C % = 63.55; H % = 6.00; N % = 9.26; S % = 10.60. Found: C % = 62.98; H % = 5.91; N % = 9.02; S % = 10.25.

EXAMPLE 25

Methyl-[8-methyl-6-(2-methoxyphenyl)-3,4-dihydro-2H,6H-pyrimido[2,1-b][1,3]thiazine-7-carboxylate]

29.3 g (0.1 mole) of methyl-[6-methyl-4-(2-methoxyphenyl)-1,2,3,4-tetrahydro-2-pyrimidinethione-5-carboxylate] and 30.3 g (0.15 mole) of 1,3-dibromopropane are reacted as described in Example 1 for 15 hours. Then the reaction mixture is evaporated, the precipitated crystals are filtered, washed with ether and dried.

Thus 20.9 g (62.9%) of the desired compound are obtained.

M.p.: 133° to 135° C.

Analysis for the Formula $C_{17}H_{20}N_2O_3S$ (332.42):
Calculated: C % = 61.42; H % = 6.06; N % = 8.43; S % = 9.64. Found: C % = 62.12; H % = 6.20; N % = 8.34; S % = 9.48.

EXAMPLE 26

Ethyl-[3,8-dimethyl-6-(3-nitrophenyl)-3,4-dihydro-2H,6H-pyrimido[2,1-b][1,3]thiazine-7-carboxylate]

32.1 g (0.1 mole) of ethyl-[6-methyl-4-(3-nitrophenyl)-1,2,3,4-tetrahydro-2-pyrimidinethione-5-carboxylate] and 19.7 g (0.115 mole) of 2-methyl-1,3-chlorobromopropane are reacted as described in Example 6 for 15 hours. The residue is crystallized from water, filtered and dried.

Thus 19.5 g (51.9%) of the desired compound are obtained.

M.p.: 124° to 126° C.

Analysis for the Formula $C_{18}H_{21}N_3O_4S$ (375.446): Calculated: C %=57.58; H %=5.64; N %=11.19; S %=8.54. Found: C %=56.48; H %=5.73; N %=11.18; S %=8.73.

EXAMPLE 27

Methyl-[6-(4-dimethylaminophenyl)-8-methyl-3,4-dihydro-2H,6H-pyrimido[2,1-b][1,3]thiazine-7-carboxylate 30.5 g (0.1 mole) of methyl-[4-(4-dimethylaminophenyl)-6-methyl-1,2,3,4-tetrahydro-2-pyrimidinethione-5-carboxylate] and 30.3 g (0.15 mole) of 1,3-dibromopropane are reacted as described in Example 14 for 32 hours. The residue is crystallized from water, filtered and dried.

Thus 26.6 g (77%) of the desired compound are obtained.

M.p.: 128° to 130° C.

Analysis for the Formula $C_{18}H_{23}N_3O_2S$ (345.463): Calculated: C %=62.58; H %=6.71; N %=12.16; S %=9.28. Found: C %=62.50; H %=6.76; N %=12.11; S %=9.14.

EXAMPLE 28

Ethyl-[6-(4-chloro-3-nitrophenyl)-8-methyl-3,4-dihydro-2H,6H-pyrimido[2,1-b][1,3]thiazine-7-carboxylate]

35.6 g (0.1 mole) of ethyl-[4-(4-chloro-3-nitrophenyl)-6-methyl-1,2,3,4-tetrahydro-2-pyrimidinethione-5-carboxylate] and 30.3 g (0.15 mole) of 1,3-dibromopropane are reacted as described in Example 14 for 13 hours. The residue is crystallized from water, filtered and dried.

Thus 36.4 g (92%) of the desired compound are obtained.

M.p.: 126° to 128° C.

Analysis for the Formula $C_{17}H_{18}ClN_3O_4S$ (395.861): Calculated: C %=51.58; H %=4.58; N %=10.61; Cl %=8.96; S %=8.10. Found: C %=51.08; H %=4.65; N %=10.32; Cl %=8.95; S %=8.00.

EXAMPLE 29

Methyl-[6-(3-hydroxy-4-methoxyphenyl)-8-methyl-3,4-dihydro-2H,6H-pyrimido[2,1-b][1,3]thiazine-7-carboxylate]

30.8 g (0.1 mole) of methyl-[4-(3-hydroxy-4-methoxyphenyl)-6-methyl-1,2,3,4-tetrahydro-2-pyrimidinethione-5-carboxylate] and 30.3 g (0.15 mole) of 1,3-dibromopropane are reacted as described in Example 14 for 30 hours. Then it is cooled, the precipitated crystals are filtered, washed with water and dried.

Thus 21.9 g (65.1%) of the desired compound are obtained.

M.p.: 275° to 277° C.

Analysis for the Formula $C_{16}H_{20}N_2O_4S$ (336.408): Calculated: C %=57.13; H %=5.99; N %=8.33; S %=9.53. Found: C %=56.98; H %=6.05; N %=8.28; S %=9.45.

EXAMPLE 30

Methyl-(4,6-dimethyl-1,2,3,4-tetrahydro-2-pyrimidinethione-5-carboxylate)

13.2 g (0.3 mole) of acetaldehyde, 22.8 (0.3 mole) of thiourea and 34.8 g (0.3 mole) of methyl acetoacetate are reacted in 100 ml of an isopropanol solution containing 15% of hydrogen chloride for 12 hours at room temperature. Then the suspension is cooled, filtered, the filtrate is washed with isopropanol and dried.

Thus 30 g (50%) of the desired compound are obtained.

M.p.: 203° to 206° C.

Analysis for the Formula $C_8H_{12}O_2S$ (200.257): Calculated: C %=47.98; H %=6.04; N %=13.99; S %=16.0. Found: C %=48.05; H %=5.98; N %=13.87; S %=15.59.

EXAMPLE 31

Methyl-(4-ethyl-6-methyl-1,2,3,4-tetrahydro-2-pyrimidinethione-5-carboxylate)

17.4 g (0.3 mole) of propionaldehyde, 22.8 g (0.3 mole) of thiourea and 34.8 g (0.3 mole) of methyl acetoacetate are reacted as described in Example 30 for 35 hours. Then the reaction mixture is cooled, filtered, the filtrate is washed and dried.

Thus 12.8 g (20%) of the desired compound are obtained.

M.p.: 180° to 182° C.

Analysis for the Formula $C_9H_{14}N_2O_2S$ (214.284): Calculated: C %=50.45; H %=6.58; N %=13.07; S %=14.96. Found: C %=50.52; H %=6.81; N %=12.85; S %=14.95.

EXAMPLE 33

Ethyl-(4,6-dimethyl-1,2,3,4-tetrahydro-2-pyrimidinethione-5-carboxylate)

13.2 g (0.3 mole) of acetaldehyde, 39.0 g (0.3 mole) of ethyl acetoacetate and 22.8 g (0.3 mole) of thiourea are reacted as described in Example 30 for 15 hours. The reaction mixture is cooled, filtered, the filtrate is washed and dried.

Thus 30 g (46.7%) of the desired compound are obtained.

M.p.: 198° to 200° C.

Analysis for the Formula $C_9H_{14}N_2O_2S$ (214.284): Calculated: C %=50.45; H %=6.58; N %=13.07; S %=14.96. Found: C %=50.45; H %=6.58; N %=13.10; S %=14.80.

EXAMPLE 34

Ethyl-(4-ethyl-6-methyl-1,2,3,4-tetrahydro-2-pyrimidinethione-5-carboxylate)

17.4 g (0.3 mole) of propionaldehyde, 22.8 g (0.3 mole) of thiourea and 39 g (0.3 mole) of ethyl acetoacetate are reacted in 400 ml of an isopropanol solution containing 15% hydrogen chloride for 35 hours. Then the reaction mixture is evaporated in vacuo, the residue is crystallized from water, filtered and dried.

Thus 20.5 g (30%) of the desired compound are obtained.

M.p.: 143° to 145° C.

Analysis for the Formula $C_{10}H_{16}N_2O_2S$ (228.312): Calculated: C %=52.9; H %=7.07; N %=12.50; S %=14.37. Found: C %=52.61; H %=7.06; N %=12.27; S %=14.04.

EXAMPLE 35

Ethyl-(4-methyl-6-phenyl-1,2,3,4-tetrahydro-2-pyrimidinethione-5-carboxylate)

13.2 g (0.3 mole) of acetaldehyde, 22.8 g (0.3 mole) of thiourea and 57.7 g (0.3 mole) of benzoylacetic acid ethyl ester are reacted as described in Example 30 for 30 hours. The reaction mixture is cooled, filtered, the filtrate is washed and dried.

Thus 31.5 g (38%) of the desired compound are obtained.

M.p: 220° to 235° C.

Analysis for the Formula $C_{14}H_{16}N_2O_2S$ (276.356): Calculated: C %=60.85; H %=5.83; N %=10.14; S %=11.60. Found: C %=60.47; H %=5.76; N %=10.11; S %=11.72.

EXAMPLE 36

Ethyl-(4-ethyl-6-phenyl-1,2,3,4-tetrahydro-2-pyrimidinethione-5-carboxylate)

17.4 g of propionaldehyde, 22.8 g (0.3 mole) of thiourea and 57.7 g (0.3 mole) of benzoylacetic acid ethyl ester are reacted as described in Example 30 for 30 hours. The reaction mixture is cooled, filtered, the filtrate is washed and dried.

Thus 30.5 g (35%) of the desired compound are obtained.

M.p.: 219° to 221° C.

Analysis for the Formula $C_{15}H_{18}N_2O_2S$ (290.382): Calculated: C %=62.05; H %=6.25; N %=9.65; S %=11.04. Found: C %=62.20; H %=6.31; N %=9.74; S %=11.10.

EXAMPLE 37

4-Undecyl-6-methyl-1,2,3,4-tetrahydro-2-pyrimidinethione-5-carboxylic anilide 55.3 g (0.3 mole) of lauric aldehyde, 22.8 g (0.3 mole) of thiourea and 53.2 g (0.3 mole) of acetoacetic anilide are reacted as described in Example 30 for 30 hours. The reaction mixture is cooled, filtered, the filtrate is washed and dried.

Thus 29 g (24.1%) of the desired compound are obtained.

M.p.: 158° to 160° C.

Analysis for the Formula $C_{23}H_{35}N_3OS$ (401.614): Calculated: C %=68.79; H %=8.78; N %=10.46; S %=7.98. Found: C %=67.46; H %=8.94; N %=10.12; S %=7.82.

What we claim is:

1. A member of the group consisting of dihydropyrimidothiazine derivatives of Formula I,

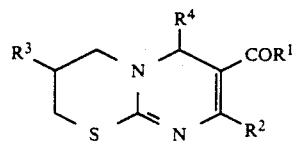

wherein
$R^1$ represents $C_{1-6}$ alkoxy, amino or phenylamino,
$R^2$ stands for $C_{1-6}$ alkyl or phenyl,
$R^3$ represents hydrogen or $C_{1-6}$ alkyl, and
$R^4$ denotes $C_{1-11}$ alkyl or phenyl optionally bearing one or more identical or different substituent(s) selected from halogen, nitro, amino, di-($C_{1-6}$ alkyl)-amino, $C_{1-6}$ alkyl, $C_{1-6}$ alkoxy and hydroxy,
and pharmaceutically acceptable acid addition salts thereof.

2. A compound according to claim 1, wherein $R^1$ stands for methoxy, ethoxy or amino, $R^2$ denotes methyl or phenyl, $R^3$ stands for hydrogen, and $R^4$ represents methyl or phenyl wherein the latter carries one or more identical or different methoxy, halogen or nitro substituent(s).

3. A compound selected from the group consisting of ethyl-[6-(4-dimethylaminophenyl)-8-methyl-3,4-dihydro-2H,6H-pyrimido[2,1-b][1,3]thiazine-7-carbonxylate], methyl-[8-methyl-6-(2-methoxyphenyl)-3,4-dihydro-2H,6H-pyrimido[2,1-b][1,3]thiazine-7-carboxylate], methyl-[6-(3,4-dichlorophenyl)-8-methyl-3,4-dihydro-2H,6H-pyrimido[2,1-b][1,3]thiazine-7-carboxylate], methyl-[6-(4-chloro-3-nitrophenyl)-8-methyl-3,4-dihydro-2H,6H-pyrimido[2,1-b][1,3]thiazine-7-carboxylate] and pharmaceutically acceptable acid addition salts thereof.

4. A pharmaceutical composition comprising as an active ingredient an antianginally and/or antiinflammatorily effective amount of at least one compound of Formula I according to claim 1, or a pharmaceutically acceptable salt thereof.

5. A method of antianginal and/or antiinflammatory treatment, which comprises administering to a patient an antianginally and/or antiinflammatory effective amount of a compound of Formula I according to claim 1, or a pharmaceutically acceptable salt thereof.

* * * * *

UNITED STATES PATENT AND TRADEMARK OFFICE
CERTIFICATE OF CORRECTION

PATENT NO. : 5,071,849

DATED : December 10, 1991

INVENTOR(S) : Daniel Boszing et al.

It is certified that error appears in the above-identified patent and that said Letters Patent is hereby corrected as shown below:

Title page, at [75], add the following inventors:

--Pal Benko; Eniko Szirt--

Signed and Sealed this

Twentieth Day of April, 1993

*Attest:*

MICHAEL K. KIRK

*Attesting Officer*      *Acting Commissioner of Patents and Trademarks*